United States Patent
Carpenter

(10) Patent No.: US 7,424,376 B2
(45) Date of Patent: Sep. 9, 2008

(54) PRECISE PRESSURE MEASUREMENT BY VIBRATING AN OVAL CONDUIT ALONG DIFFERENT CROSS-SECTIONAL AXES

(76) Inventor: Brent L. Carpenter, 209 Mulligan Lake Dr., Mead, CO (US) 80542

( * ) Notice: Subject to any disclaimer, the term of this patent is extended or adjusted under 35 U.S.C. 154(b) by 0 days.

(21) Appl. No.: 10/535,329

(22) PCT Filed: Jul. 25, 2003

(86) PCT No.: PCT/US03/23173

§ 371 (c)(1),
(2), (4) Date: May 18, 2005

(87) PCT Pub. No.: WO2004/011894

PCT Pub. Date: Feb. 5, 2004

(65) Prior Publication Data

US 2006/0173639 A1    Aug. 3, 2006

Related U.S. Application Data

(60) Provisional application No. 60/398,450, filed on Jul. 25, 2002.

(51) Int. Cl.
*G01F 17/00* (2006.01)
(52) U.S. Cl. .................................. 702/50
(58) Field of Classification Search .............. 702/50
See application file for complete search history.

(56) References Cited

U.S. PATENT DOCUMENTS

| | | |
|---|---|---|
| 3,800,413 A | 4/1974 | Frick |
| 3,808,480 A | 4/1974 | Johnston |
| 3,863,505 A | 2/1975 | Moffatt |
| 4,048,846 A | 9/1977 | Catherall |
| 4,149,422 A | 4/1979 | Olsen et al. |
| 4,232,544 A | 11/1980 | Stansfeld |
| 4,311,053 A | 1/1982 | Cucci |
| 4,329,775 A | 5/1982 | Olsen et al. |
| 5,231,881 A | 8/1993 | Lew |
| 5,317,917 A | 6/1994 | Dufour |
| 5,473,949 A | 12/1995 | Cage et al. |
| 5,731,527 A * | 3/1998 | Van Cleve ............ 73/861.355 |

(Continued)

FOREIGN PATENT DOCUMENTS

DE    4239546    5/1994

(Continued)

OTHER PUBLICATIONS

PCT/US03/23173 International Search Report; Oct. 2003.

*Primary Examiner*—Bryan Bui
*Assistant Examiner*—Aditya S Bhat
(74) *Attorney, Agent, or Firm*—Lathrop & Gage LC

(57) ABSTRACT

A conduit (106), with geometry designed to enhance pressure sensitivity, is vibrated at resonance in two modes along different cross-sectional axes (a, b). Measuring the change in the frequency ratio squared of the modes yields a substantially linear relationship to pressure that is substantially immune to other material properties and other environmental factors. Moments of inertia in different cross-sectional axes are related to pressure as a result of the elliptical or oral cross section of the conduit (106).

23 Claims, 9 Drawing Sheets

U.S. PATENT DOCUMENTS

| | | | |
|---|---|---|---|
| 5,734,112 A * | 3/1998 | Bose et al. | 73/861.56 |
| 5,770,805 A * | 6/1998 | Castel | 73/861.04 |
| 6,230,104 B1 | 5/2001 | Shelley et al. | |
| 6,301,973 B1 | 10/2001 | Smith | |
| 6,513,392 B1 * | 2/2003 | Barger et al. | 73/861.356 |
| 6,636,815 B2 * | 10/2003 | Keilty et al. | 702/45 |
| 2003/0055580 A1 * | 3/2003 | Normen | 702/45 |

FOREIGN PATENT DOCUMENTS

| | | |
|---|---|---|
| DE | 4239546 A | 5/1994 |
| JP | 57066327 | 4/1982 |
| JP | 57066327 A | 4/1982 |

* cited by examiner

Figure 8 - Model And Actual Data Relating Moment Of Inertia Ratio To Pressure

PRECISE PRESSURE MEASUREMENT BY VIBRATING AN OVAL CONDUIT ALONG DIFFERENT CROSS-SECTIONAL AXES

CROSS REFERENCE TO RELATED APPLICATIONS

This application is related to U.S. Provisional Patent Application No. 60/398,450 (filed Jul. 25, 2002; the "provisional") and claims the benefit of the earlier filing date of the provisional.

PROBLEM

1. Field of the Invention

This invention relates to systems and methods for determining pressure and other properties of materials conveyed through a conduit. More specifically, the conduit is vibrated to yield a pressure value that is substantially immune to exogenous factors.

2. Discussion of the Related Art

There are numerous systems reported in the prior art for determining a pressure measurement, such as Bernoulli devices and piezoelectric devices. Bernoulli devices may disadvantageously require penetration into tubing; piezoelectric devices may be affected by material properties such as density, temperature, and viscosity. Complex installation requirements and the need to periodically recalibrate for particular operating are problematic in the art.

One example of a prior art system includes a diaphragm sensor, as disclosed in U.S. Pat. No. 3,800,413 (issued Apr. 2, 1974) and in U.S. Pat. No. 3,808,480 (issued Apr. 30, 1974). These devices are limited in absolute accuracy by the inherent non-linearity of converting pressure to a mechanical displacement followed by converting displacement to an electronic signal required for a user interface. Diaphragm pressure sensors rely on a thin member or diaphragm to convert pressure to displacement. The diaphragm is supported at its periphery by a housing. The housing distorts with changes in pressure, temperature, and installation factors. This distortion puts exerts undesirable forces on the diaphragm either changing its displacement or its responsiveness to applied pressure. These effects make the relationship between pressure and displacement inherently non-linear which, in turn, restricts the useful measurement range. Typical diaphragm pressure sensors are limited to measuring pressures that are no more than ⅓ to 3 times the calibration standard. Accurate measurement beyond this range can only be accomplished by re-calibration or by employing cascaded pressure sensors, each calibrated to cover overlapping pressure ranges. Both approaches add cost and complexity not valued by industry.

Pressure sensitivity is directly related to diaphragm geometry, material of construction, and thickness. These diaphragms are not typically suited for direct contact with industrial fluids. Corrosive or aggressive industrial fluids require a coupling fluid to safely convey pressure to the diaphragm. Thermal expansion, viscosity changes, and compressibility characteristics of the coupling fluid exert unpredictable pressures on the diaphragm. The resulting dependency on uncontrollable environments factors and the inability to measure pressure precisely over operating conditions commonly found in industry further limit the accuracy of these devices. Other prior art systems attempt to minimize this effect by selecting low viscosity oils as disclosed in U.S. Pat. No. 4,329,775 (issued May 18, 1982; the "'775 patent"); however, the use of low viscosity oils adds cost and complexity without substantially improving performance. For example, the use of low viscosity oils reduces the useful temperature range of the sensor to less than requisite because the oils have undesirable property changes corresponding to temperatures outside a narrow temperature range. Fluid as used herein can refer to a gas, liquid, suspension, foam, slurry and/or another material capable of flowing through a conduit. Suspension and slurry are known to those skilled in the art.

Mechanical strain to electrical signal conversion contributes to non-linearity and reduced accuracy due to the low voltage analog signals and poor signal to noise ratio (SNR). In an attempt to overcome the low analog signal limitations of diaphragm pressure transducers, beams or wires have been mechanically coupled to the diaphragm. The beam or wire is vibrated at its resonant frequency. The diaphragm affects the resonant frequency by translating pressure changes into load changes. The '775 patent, U.S. Pat. No. 4,149,422 (issued Apr. 17, 1979), and U.S. Pat. No. 5,231,881 (issued Aug. 3, 1993) each discloses the use of vibrating wires coupled to a diaphragm. U.S. Pat. No. 4,311,053 (issued Jan. 19, 1982) and U.S. Pat. No. 5,317,917 (issued Jun. 7, 1994) discloses a use of a rigid beam functioning in a similar fashion.

While these patents recognized the value of frequency measurement to overcome small signal noise limitations, they fail to address the inaccuracy associated with the diaphragm and housing. Reliability issues are associated with each addition of mechanical components, interfaces and calibration requirements. Additional sources of error in the diaphragm devices include impractical sensor constructions. For example, additional mechanical components and interfaces add vibration damping and introduce secondary frequencies that cause uncertainty in the resonant frequency. As another example, construction is impractical because fragile beams or wires are bonded to fragile diaphragms. A strong bond is necessary for reliability and low damping; however, such bonding stiffens or otherwise reduces the pressure sensitivity of the diaphragm. The tradeoff between sensitivity and reliability limits practical industrial applications of these devices.

U.S. Pat. No. 3,863,505 (issued Feb. 4, 1975; the "'505 patent"), U.S. Pat. No. 4,048,846 (issued Sep. 20, 1977; the "'846 patent"), and U.S. Pat. No. 4,232,544 (issued Nov. 11, 1980) each recognize the limitations of diaphragms and opt to use thin wall tubings or rings having circular cross sections that are vibrated in either a flexural or radial mode. Unfortunately these devices have poor pressure sensitivity. They are affected by temperature and fluid density, making independent measurements and calibration impossible. In general, these devices have been created to address pressure measurements under specific conditions and are generally not suited for use in an industrial environment. The '505 patent also discloses that modes of vibration in a tubing having circular cross section are pressure dependent causing erratic operation over some pressure ranges. The '846 patent shows non-linear behavior over all but a narrow pressure range caused by changes in a gearing factor. The limited operating range, poor linearity, and dependency on other fluid properties have undermined industrial acceptance of pressure sensors based on this technology.

U.S. Pat. No. 5,473,949 (issued Dec. 12, 1995; the "'949 patent") and U.S. Pat. No. 5,734,112 (issued Mar. 31, 1998; the "'112 patent") added pressure measurement capability to mass flow sensors where the operation is based on the Coriolis principle. Both the '949 and the '112 patents take advantage of vibrations associated with making a Coriolis mass flow measurement to add a Coriolis-based pressure measurement capability. Pressure is measured to compensate the mass flow measurement but can be made available as an additional measurement. U.S. Pat. No. 6,301,973 (issued Oct. 16, 2001) applies this pressure functionality in developed a non-intrusive apparatus for measuring gas pressure. In all cases, pressure accuracy is limited for the same reasons disclosed in the '505 patent, the '846 patent, and in the '544 patent.

The devices disclosed in the '505 patent, '846 patent, '544 patent, the '949 patent, and the '112 patent employ a tubular component or structure with a circular cross-section. Pressure sensitivity in these devices is low and linearity is poor, essentially because pressure has little effect on resonant frequency of Coriolis meter tubes and, thus, does not allow for a separation of changes in resonance frequency due to pressure from other variables. Additionally, complex signal processing electronics and algorithms are needed to extract pressure from the inherent noise, thereby adding cost, increasing calibration difficulties, and reducing accuracy. The prior art discloses a variety of systems to determine pressure. All have shown limitations in terms of linearity, immunity to non-pressure material properties, and/or environmental factors. Hence, there is a need to provide accurate pressure measurements over a wide range of pressures, substantially immune to such non-pressure related variables.

SOLUTION

The present invention provides a solution to the above and other problems and advances the art by providing for pressure over a wide range by using strain in a flow tube or conduit. Use of a unique conduit geometry, resonant frequency measurements, and direct coupling of fluid to the conduit provide improved pressure sensitivity and good immunity to exogenous variables. In one embodiment, complex algorithms, signal processing electronics, and filters are not necessarily required, due to the improved pressure sensitivity, inherent linearity and low noise. Accordingly, the systems and methods described herein simplify design, reduce cost, and improve reliability.

In one embodiment, the need to compensate for temperature, flow rate, density, and installation factors is reduced, adding to the reliability and accuracy of the measurement. Calibration is simplified since a large variety of readily available fluids can be used. Once calibrated, pressure measurements can be made on other fluids and under varying conditions without an appreciable loss of precision. Since the pressure response is nearly linear over a wide range, calibration can be accomplished with as few as two points with the option of using additional calibration points to further enhance accuracy. Although not needed for determining pressure, density and temperature information is also available allowing better characterization of the fluid in question without the need for additional instrumentation.

In one embodiment, coupling fluids are not needed because the sensor directly interacts with the fluid under measurement. Accordingly, fewer parts may be used, which may also improve reliability. In another embodiment, applying pressure to the outside of the conduit yields substantially the same response as applying pressure to the inside. Additionally, the absence of appreciable hysteresis may allow the sensor to accurately determine flow rate when combined with differential pressure volumetric devices. In an embodiment where a conduit has an oval-shaped cross-section, or, preferably, an elliptical-shaped cross-section, the cross-section presents a major axis and a minor axis. Mathematics shown below confirm that pressure may be calculated as the displacement on any one of the major and minor axis using the center of the cross-section as a point of reference.

In one embodiment, pressure sensing operation is based on resonant vibration of a conduit that either contains or is surrounded by a fluid. The conduit is tubular having an elliptical or an oval cross-section. The conduit may be straight, bent, or curved over its length. The conduit is mechanically designed so that it can be electronically vibrated in two directions and may be vibrated at or near resonance. Resonance as used herein means vibrating a conduit in a particular direction at its natural frequency of vibration such that the power required for vibration is minimized. Pressure may be calculated as a function of natural frequency along one or more axes, as described below. Although the following discussion pertains to mathematical and physical principles and may be availed to enhance pressure sensing operations, the sensor in one embodiment is calibrated using empirical data that relates a ratio of frequencies along axes of a conduit to pressure.

The conduit is vibrated in two orthogonal directions, or modes, aligned to the major and minor axis of the cross-section. The conduit may be essentially vibrated in either a hoop direction or a bending direction. Bending direction as used herein refers to deflection of an essentially straight conduit into a slight curve in response to force acting transversely to the longitudinal axis. Hoop direction as used herein refers to deflection of a conduit cross-section in response to a radial force that squeezes the conduit with little or no deflection of the longitudinal axis. Hoop directions and bending directions as used herein are known to those skilled the art.

The contact between fluid and conduit is such that the fluid pressure acts to deform the conduit according to principles of structural dynamics described below.

The frequency for each vibrational mode can be described by Eq. 1.

$$f = \frac{1}{2\pi}\sqrt{\frac{xEI}{L^3(M+ym)}},  \quad (Eq.\ 1)$$

where f is the resonant frequency of vibration, E is the modulus of elasticity, I is the inertial moment, and L is length of the conduit. The m term represents the combined and distributed mass of the conduit and fluid whose properties are to be measured. M, L, x, and y are constants that are predetermined as a matter of design choice.

In an embodiment where the conduit is elliptical in cross-section and vibrated in two orthogonal directions, Eq. 1 can be used to describe resonance in each direction. The resonant frequency in each direction will be different since I terms are different owing to the elliptical cross-section of the conduit. The conduit will have a higher I (and therefore a higher frequency) when vibrated in the direction parallel to the major axis of the cross-section as opposed its minor axis. Assigning $I_a$ as the moment of inertia related vibration in a direction parallel to the major axis and $I_b$ to the minor axis, an equation can be derived from Eq. 1 as applied to each axis to reveal a frequency ratio relationship to an inertial moment ratio. Accordingly, Eq. 2 shows the ratio of the resonant frequency in the a to b directions and how it relates to the ratio of inertial moment for the corresponding axes.

$$\frac{f_a}{f_b} = \frac{\frac{1}{2\pi}\sqrt{\frac{xEI_a}{(M+ym)L^3}}}{\frac{1}{2\pi}\sqrt{\frac{xEI_b}{(M+ym)L^3}}} = \sqrt{\frac{I_a}{I_b}}, \text{ where} \quad \text{(Eq. 2)}$$

$I_a$ and $I_b$ are related to pressure as a result of the elliptical cross section of the tube. One possible method to establish the relationship is to consider the effect of pressure on bending moments for an elliptical cross section, followed by relating bending moments to deflection, and then followed by relating changes in deflection to changes in moment of inertia. For example, consider a conduit with an elliptical cross section where the major axis has the dimension $2a$ and the minor axis has the dimension $2b$. The relationship between pressure and bending moment has been defined by "Strength of Materials," S. Timoshenko, D. Van Nostrand Company, Inc., 1930 and referenced by "Roark's Formulas for Stress & Strain, Sixth Edition," W. C. Young, McGraw-Hill Book Company, 1989. Eq. 3 shows that the bending moment ($M_B$) is a linear function of pressure (P).

$$M_B = Ka^2 P, \quad \text{(Eq. 3)}$$

where half the major axis dimension (a) and the proportionality constant (K) are predetermined as a matter of design choice.

Changes in the major axis with pressure are relatively small and can be neglected for a first approximation model. The proportionality constant (K), and therefore the bending moments, are opposite in sign at the major and minor axis inflection points indicating that the elliptical cross section will become more circular as internal pressure is increased. With the application of internal pressure, the resulting bending moments will cause a decrease in the major axis (a) and a decrease in the moment of inertia ($I_a$) about the minor axis. Simultaneously the minor axis (b) will increase causing an increase in the moment of inertia ($I_b$) about the major axis. By symmetry, external pressure will cause an equal but opposite change in bending and inertial moments.

Displacement is related to the bending moments through elastic approximation having negligible error. Considering half the elliptical cross section as a beam with bending moments, the change in deflection can be approximated, as shown in Eq. 4.

$$\delta_b \approx M_B \left( \frac{a^2}{2EI_s} \right), \quad \text{(Eq. 4)}$$

where $\delta_b$ is the minor axis displacement, $M_B$ is the bending moment as defined by Eq. 3, a is one half the major axis dimension, E is the modulus of elasticity, and $I_s$ is the inertial moment of a beam section. Those skilled in the art will recognize that $I_s$ may generally be defined by considering the geometry of the half elliptical section as a beam with moments applied at the major or minor axis inflection points. $I_s$ should not be confused with $I_a$ or $I_b$ where the latter are the moments of inertia for the conduit as a whole. E is the elastic modulus of the tube material. A similar equation can be written for major axis displacement ($\delta_a$) by substituting b for a in Eq. 4. The $M_B$ term will be negative in this case due to the sign change of K in Eq. 3. The negative displacement indicates that the major axis (a) will decrease with increasing internal pressure.

Once the deflections are known, the respective moments of inertia can be calculated, as shown in Eq. 5.

$$I_b = \frac{\pi}{4}((a+\delta_a)(b+\delta_b)^3 - ((a+\delta_a - t)(b+\delta_b - t)^3), \quad \text{(Eq. 5)}$$

where a is one half the major axis of the cross section, b is one half the minor axis, and t is the conduit wall thickness. Interchanging the a and b terms will yield a similar equation for $I_a$. Accordingly, Eqs. 3, 4, and 5 may describe the relationship between pressure and moment of inertia terms ($I_a$ and $I_b$).

An increase in internal pressure causes a decrease in $I_a$ and an increase in $I_b$, as a result of the pressure forcing the tube to become more round. When evaluated from a frequency perspective, $f_a$ will decrease and $f_b$ will increase. Therefore, the frequency ratio defined in Eq. 2 decreases with increasing internal pressure. It should be noted that the frequency ratio can not be less than one since at this point the conduit will have a circular cross-section.

Taking the ratio of $f_a$ to $f_b$ cancels common terms as shown in Eq. 2. Elimination of E, M, and m terms implies that the ratio is independent of fluid density and temperature. Since density and temperature are not significant factors, calibration can be conducted on any fluid and under any conditions while maintaining accuracy. For example, the pressure sensor may be calibrated on water and used on another fluid (and at other temperatures) without significant changes in accuracy.

The application of an axial force, such as that which occurs in installing a sensor in a pipeline, alters both frequency terms in nearly equal proportion without substantially altering the ratio. Sensors built on this principal typically show immunity to mounting conditions and orientation. This is a distinct advantage over the prior art where pressure measurement is sensitive to density, orientation, temperature, and installation factors.

Density can be derived by considering the mass term of Eq. 1. The relationship between density, frequency, and temperature is well known in the art. For example, "DMS Density Monitoring System," Micro Motion Inc., September 1988 has defined the relationship between frequency and fluid density as shown by Eq. 6.

$$\rho = K_1 t_c T^2 - K_2, \quad \text{(Eq. 6)}$$

where $\rho$ is the fluid density, $K_1$ and $K_2$ are density calibration factors, $t_c$ is a correction for changes in elastic modulus with temperature, and T is the period corresponding to a resonant frequency f. The equation shows that an increase in fluid density increases the period of oscillation. It is known in the art that period is also dependent upon temperature due to the temperature dependency of elastic modulus. The $t_c$ term compensates for this effect and may be determined by observing the change in period with temperature using calibration fluids with known density-temperature characteristics. Period may be replaced by resonant frequency as shown in Eq. 7.

$$\rho = K_1 t_c \left( \frac{1}{f^2} \right) - K_2. \quad \text{(Eq. 7)}$$

Eq. 7 is particularly relevant to a bent or straight tubular structure of uniform cross section, subject to vibration at or near resonance, containing a fluid of density ρ. The equation may also be relevant to a conduit with an elliptical cross section by accounting for changes in frequency due to pressure. For example, density can be derived while accounting for applied pressure by averaging $f_a$ and $f_b$. The frequency term ($f^2$) is dependent upon both density and pressure. However, $f_a$ will decrease by a small amount ($\Delta f_a$) and $f_b$ will increase by a small amount ($\Delta f_b$) with an increase in pressure. Averaging $f_a$ and $f_b$ yields a frequency term that is substantially independent of pressure as shown by Eq. 8.

$$f_{avg} = \frac{f_a - \Delta f_a + f_b + \Delta f_b}{2} = \frac{f_a + f_b}{2}, \quad \text{(Eq. 8)}$$

where $f_{avg}$ is the average frequency of $f_a$ and $f_b$. Substituting $f_{avg}$ for f in Eq. 7 yields an accurate density relationship substantially independent of pressure. The approach makes it possible to obtain independent and accurate pressure and density measurements from the same sensor.

An alternative method of determining density includes correcting Eq. 7 with a pressure correction factor ($P_c$) calculated after determining fluid pressure as shown in Eq. 9.

$$\rho = K_1 P_c t_c \left(\frac{1}{f^2}\right) - K_2, \quad \text{(Eq. 9)}$$

where ρ is the fluid density, $K_1$ and $K_2$ are density calibration factors, $t_c$ is a correction for changes in elastic modulus with temperature, $f^2$ is the measured frequency in either the "a" or "b" direction, and $P_c$ is the pressure correction factor. The pressure correction factor compensates $K_1$ in much the same way as the temperature correction factor. The pressure correction factor may be determined by measuring the change in frequency with changes in pressure during the density calibration process.

The vibration imparted to a conduit to make pressure and density measurements is also useful for Coriolis mass flow measurements. As fluid flows through a vibrating conduit, it is subject to Coriolis accelerations. The resulting Coriolis forces cause each point along the conduit to have a slightly different phase relationship. Velocity sensors (e.g., frequency sensors) or other motion detection devices, placed near the inlet and the outlet will show a phase difference proportional to the mass flow rate. Usually, the phase difference is determined as a time difference between the inlet sensor crossing a specific level relative to the outlet sensor. It is know in the art that the mass flow rate is related to this time difference by a proportionality constant as shown in Eq. 10.

$$M = c\Delta t, \quad \text{(Eq. 10)}$$

where M is the mass flow rate of the fluid, c is a proportionality constant, and $\Delta t$ is the time difference between the inlet and outlet sensors. The proportionality constant is usually determined through calibration. Its value is related to the inertial moment of the conduit and other design parameters. For an elliptical conduit designed for pressure measurement, the inertial moments differ with orientation. Furthermore the moments of inertia are dependent upon the pressure applied either inside or outside the conduit. Therefore, the proportionality constant c will have different values that depend on orientation of the inlet and outlet velocity sensors and pressure. Orientation may be set by design and pressure may be accounted for by adding a pressure compensation factor ($F_c$) to Eq. 10 as shown in Eq. 11.

$$M = c F_c \Delta t \quad \text{(Eq. 11)}$$

The pressure compensation factor ($F_c$) and the proportionality factor (c) may be determined during calibration by measuring changes in $\Delta t$ while systematically changing pressure and mass flow rate. For example, the proportionality constant may be determined by calibration at two different flow rates and a constant pressure and the pressure correction factor determined by holding the mass flow rate constant and varying pressure.

The aforementioned description provides a background for the operation of a sensor in one embodiment of invention. Those skilled in the art should appreciate that other sensors employing other techniques for evaluating pressure with a frequency ratio may fall within the scope of the invention.

In one aspect of the invention, a sensor comprises: a conduit configured for conveying a material, a vibrator configured for vibrating the conduit along a first cross-sectional axis and for vibrating the conduit along a second cross-sectional axis; a sensor configured for detecting a first frequency along the first cross-sectional axis and for detecting a second frequency along the second cross-sectional axis; and a processor configured for determining a pressure of the material based on a ratio of the first frequency and the second frequency.

In another aspect, the conduit comprises a cross-section selected from one of an elliptical shape and an oval shape.

In another aspect, the first frequency is a function of design constants, mass of the material and an elasticity of the conduit.

In another aspect, the ratio is related to the pressure through first and second inertial moments according to an equation having a form of $$\frac{(firstfrequency)^2}{(secondfrequency)^2} = \frac{I_a}{I_b},$$

where $I_a$ is the first inertial moment and $I_b$ is the second inertial moment.

In another aspect, the first inertial moment has a form of $$I_a = \frac{\pi}{4}((b+\delta_b)(a+\delta_a)^3 - ((b+\delta_b - t)(a+\delta_a - t)^3),$$

where b is a length of one half the second cross-sectional axis, $\delta_b$ is a displacement for the second cross-sectional axis, a is a length of one half the first cross-sectional axis, $\delta_a$ is a displacement for the first cross-sectional axis and t is a conduit wall thickness.

In another aspect, the pressure linearly corresponds to the ratio of the first and the second frequencies.

In another aspect, the conduit is elastically deformable to change a length of the second cross-sectional axis based on the pressure of the material.

In another aspect, the processor comprises a converter configured for receiving control signals from the sensor and for digitally converting the control signals to represent the first frequency and the second frequency.

In another aspect, the sensor comprises a temperature sensor configured for detecting a temperature of the material conveyed through the conduit and for generating a temperature control signal for processing by the processor.

In another aspect, the sensor comprises a timing controller configured for synchronizing the processing of the temperature control signal with the determining of the pressure.

In another aspect, the sensor comprises a frequency sensor configured for detecting a phase difference in at least one of the first and the second frequencies, wherein the processor is further adapted to determine a mass flow rate of the material based on the phase difference.

In one aspect of the invention, a method of measuring a property of a material conveyed through a conduit, comprises: vibrating the conduit along a first cross-sectional axis; vibrating the conduit along a second cross-sectional axis; detecting a first resonant frequency along the first cross-sectional axis in response to vibrating the conduit at the first cross-sectional axis; detecting a second resonant frequency at the second cross-sectional axis in response to vibrating the conduit along the second cross-sectional axis; and determining a pressure of the material based on a ratio of the first resonant frequency and the second resonant frequency.

In another aspect, vibrating the conduit along the first cross-sectional axis comprises vibrating the conduit along the first cross-sectional axis of an elliptically-shaped cross-section of the conduit.

In another aspect, vibrating the conduit along the first cross-sectional axis comprises vibrating the conduit along the first cross-sectional axis of an oval-shaped cross-section of the conduit.

In another aspect, determining comprises determining the pressure by linearly corresponding the pressure to a ratio of the first and the second frequencies.

In another aspect, the method further comprises conveying the material through the conduit, wherein conveying comprises elastically deforming the conduit to change a length of the second cross-sectional axis based on the pressure of the material.

In another aspect, detecting comprises converting the first resonant frequency and the second resonant frequency into digital representations of the first resonant frequency and the second resonant frequency.

In another aspect, determining comprises processing the digital representations of the first resonant frequency and the second resonant frequency to determine the pressure of the material based on the squared ratio of the first resonant frequency and the second resonant frequency.

In another aspect, the method further comprises detecting a temperature of the material and generating a temperature control signal in response to detecting the temperature.

In another aspect, the method further comprises processing the temperature control signal with the digital representations of the first resonant frequency and the second resonant frequency in a substantially synchronous manner to determine the pressure of the material.

In another aspect, the method further comprises: detecting a phase difference in at least one of the first and the second resonant frequencies; and determining a mass flow rate of the material based on the phase difference.

DETAILED DESCRIPTION

Figure 1:
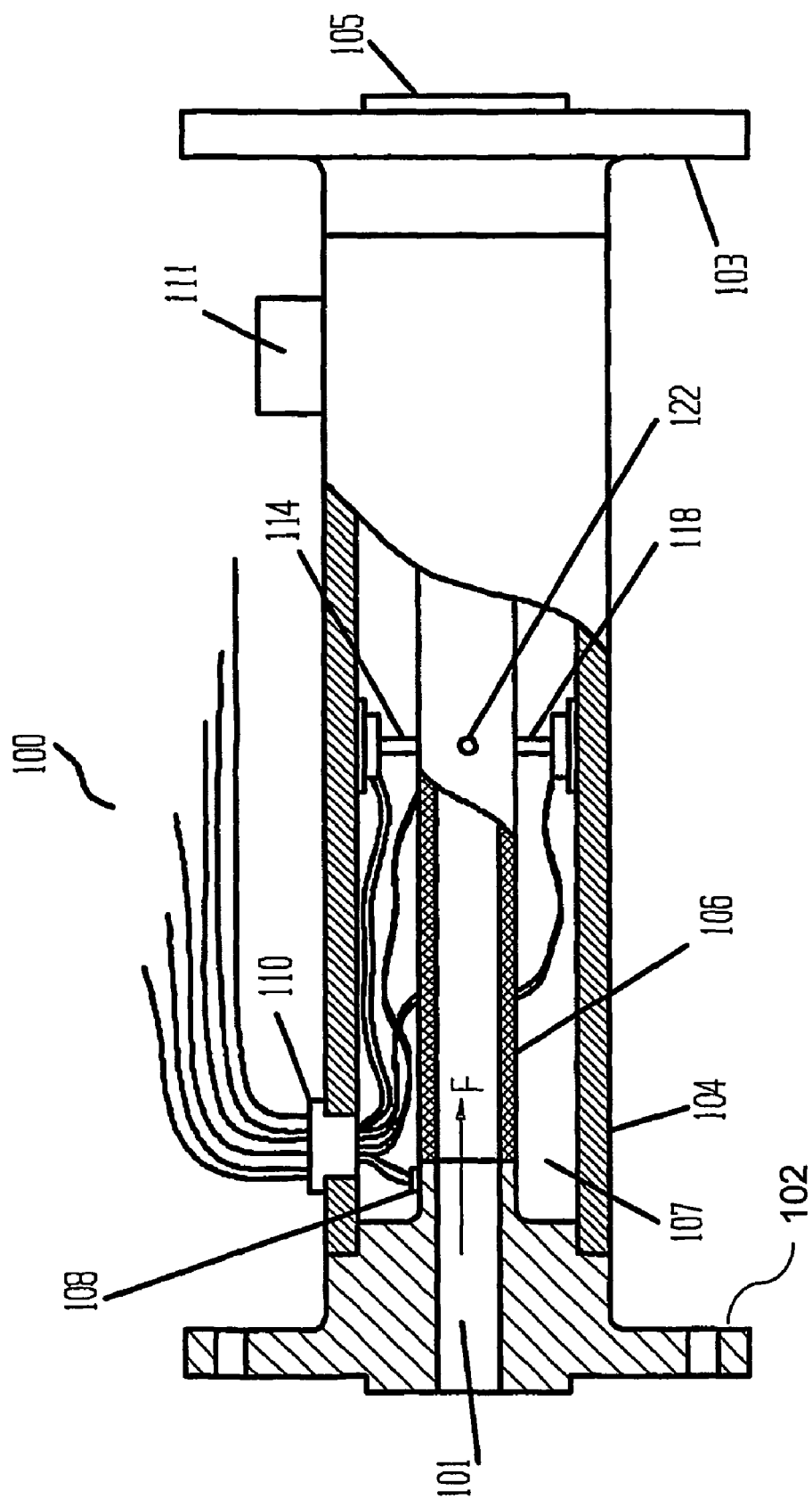
FIG. 1 depicts a sensor in one embodiment of the invention.

While the invention is amenable to various modifications and alternative forms, a specific embodiment thereof is shown by way of example in the drawings and will herein be described in detail. It should be understood that the teaching is by way of example, not of limitations to the particular form disclosed.

With reference now to the pressure figures and in particular with reference to FIG. 1, an embodiment hereof is shown in sensor 100, which may also be configured as a straight tube Coriolis flow meter, densometer, and viscosimeter. Sensor 100 is configured for determining a pressure of the fluid based on a squared ratio of detected frequencies resulting from vibration of conduit 106. In this embodiment, conduit 106 has an elliptical cross-section and is attached to ridged flanges 102 and 103. Typical wall thickness of conduit 106 would range between 0.006 inches to 0.25 inch, however, other wall thicknesses maybe used. Conduit 106 preferably comprises metal but could also comprise plastic, ceramic or composite and is not intended to be limited to the preferred embodiment. Specific dimensions and materials of construction may depend upon pressure range, sensitivity, temperature range, nature of the fluid, the application, and other design parameters. Those skilled in the art should recognize that conduit 106 is not limited to elliptical cross-sections. For example, oval-shaped cross-sections may be used as an alternative design choice.

Flange 102 provides a physical interface to a pipeline (not shown) and a conveyance 101 for a fluid F to the inside of conduit 106. Flange 103 provides a return interface 105 for the fluid to the pipeline. In one embodiment, vacuum measurement is also possible. Flanges 102/103 provide mass and rigidity so as to isolate vibration of conduit 106 from the pipeline. Isolation may improve pressure measurement accuracy by reducing uncertainty in the resonant frequency of conduit 106 brought about by interference from any existing pipeline vibration. A wide range of flanges can be employed depending upon the size and pressure rating of the piping system. Selection of flanges is well known by those skilled in the art.

In one embodiment, a housing 104 surrounds conduit 106. Housing 104 is designed for pressure containment and may provide a region 107 that is optimally filled with fluid outside conduit 106. The pressure exerted fluid in region 107 may act with substantially the same magnitude, but in an opposing direction, to the fluid F contained within conduit 106. For example, connector 111 may couple region 107 to ambient, vacuum, or fluid F at a different point in the process yielding gauge, absolute, or differential measurements respectively. As shown in this embodiment, a wire egress or feed-through 110 is placed in the housing 104 to provide connections to an electronics package (described herein below). Such a feed through 110 may be designed to maintain pressure containment capability.

Electromagnetic oscillators 114, 118, and 122, for example, coil and bar assemblies of the type shown in U.S. Pat. No. 6,230,104 (issued May 8, 2001) may attach to major and minor axes of the conduit 106 cross-section. The electromagnetic oscillators 114, 118, and 122 are configured either as drivers (i.e., vibrators) according to a frequency of a time varying voltage that minimizes power consumption to establish the natural frequency on each axis of conduit 106 or as pickoffs for vibrating in response to the driver. For example, electromagnetic oscillators 114 and 122 may be configured as pickoffs whereas electromagnetic oscillator 118 may be a driver.

In one embodiment, a Resistive Thermal Device ("RTD") 108 is attached to a thin portion of either of flanges 102/103 near, but not on, conduit 106. The RTD is configured to measure conduit 106 temperature. Conduit 106 temperature maybe used to compensate density measurements. Flanges 102/103 may be made from materials with high thermal conductivity. Alternatively, flanges 102/103 may have a "thin section" where the RTD 108 is attached so that the temperature measured is substantially representative of the fluid temperature. Fluid temperature can therefore be provided as an additional measurement.

While a single straight conduit is preferred, conduit 106 may be bent or curved. Additionally, more than one conduit 106 may be employed with fluid flowing either serially or in parallel. In such and embodiment, the design goal is to increase effective conduit length, and therefore pressure sensitivity, while maintaining a reasonably compact design or low pressure drop.

Figure 2:
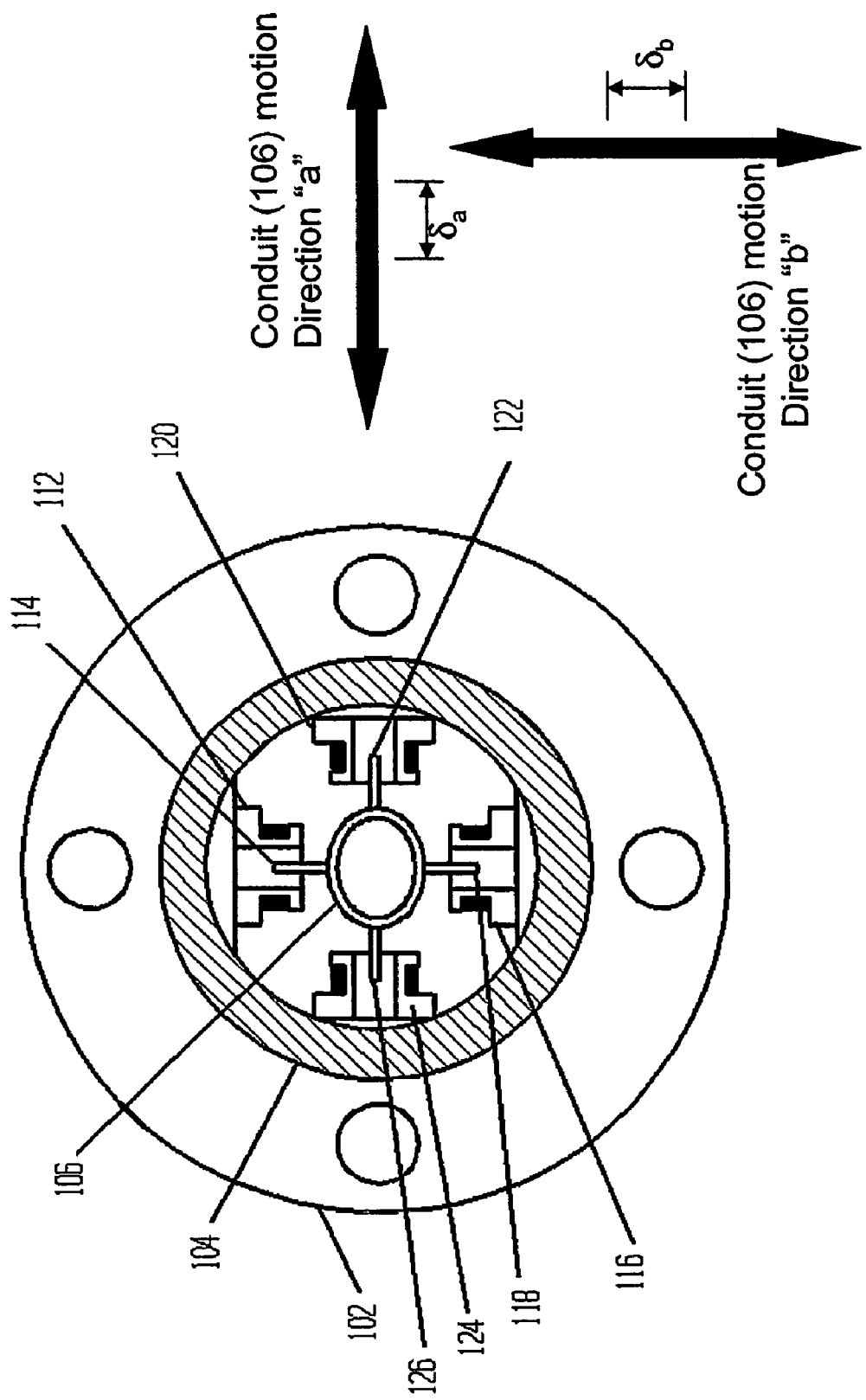
FIG. 2 shows a cross-sectional view of the embodiment shown in FIG. 1.

FIG. 2 shows a cross sectional view of the embodiment shown in FIG. 1. In this exemplary embodiment, conduit 106 has an elliptical cross section and is configured to vibrate in bending. As used herein, bending refers to deflection of conduit 106 essentially above and below its longitudinal or flow axis. Electromagnetic oscillators 114, 118, 122 and 126 are attached perpendicular to conduit 106 at the apexes of the major axis a and minor axis b by brazing, soldering, gluing or other mechanical attaching means. Attachment is such that magnets of the electromagnetic oscillators comprising magnets 114, 118, 122 and 126 and coils 112, 116, 120 and 124 are in contact with conduit 106 thereby allowing the electromagnetic oscillators and the conduit to move or vibrate substantially in unison.

The electromagnetic oscillators of 114, 118, 122 and 126 are also rigidly attached to housing 104. Each coil 112, 116, 120 and 124 surrounds one of magnets 114, 118, 122, and 126 respectively. Each magnet is positioned within a coil, e.g. magnet 116 within coil 117, to provide electromagnetic interaction. In one embodiment, the magnet and coil dimensions are designed to allow substantially free vibration of the conduit impeded by collision between magnet and coil assemblies.

Conduit 106 is designed to vibrate in a direction parallel to the major axis of the elliptical cross section ("direction a") and vibrate in a direction parallel to the minor axis of the elliptical cross section ("direction b"). These vibrational modes may be in addition to other vibrational modes.

The electromagnetic oscillators 114, 118 (axis b), 122 and 126 (axis a) are designed to operate in pairs with one operating as an electromagnetic driver and the other magnet acting as a velocity sensor or pickoff. For example, electromagnetic oscillator 118 may be a driver and electromagnetic oscillator 114 a pickoff, or vice versa. It is also possible to have one electromagnetic oscillator 118, and eliminate the pickoff 114, choosing, instead, to sense frequency as back electromotive force ("EMF") in electromagnetic oscillator 118 form a velocity sensor positioned to detect motion of conduit 106 in direction b.

FIGS. 1 and 2 show a pressure sensor 100 embodiment for measuring pressure in one embodiment. Other embodiments may include substitution of an oval cross section for the elliptical cross section shown for conduit 106. Additionally, the cross section may be configured to vibrate in a "hoop mode" that essentially squeezes conduit 106 at the major and minor axes in another embodiment. While discussed with respect to a particular geometrical configuration, namely the configuration of the a axis and the b axis, those skilled in the art should readily recognize that other configurations may fall within the scope and spirit of the invention. For example, conduit 106 may be rotated such that the a axis and the b axis are angularly displaced with respect to the embodiment as shown. Accordingly, the embodiment of sensor 100 is intended to be merely illustrative in nature.

Figure 3:
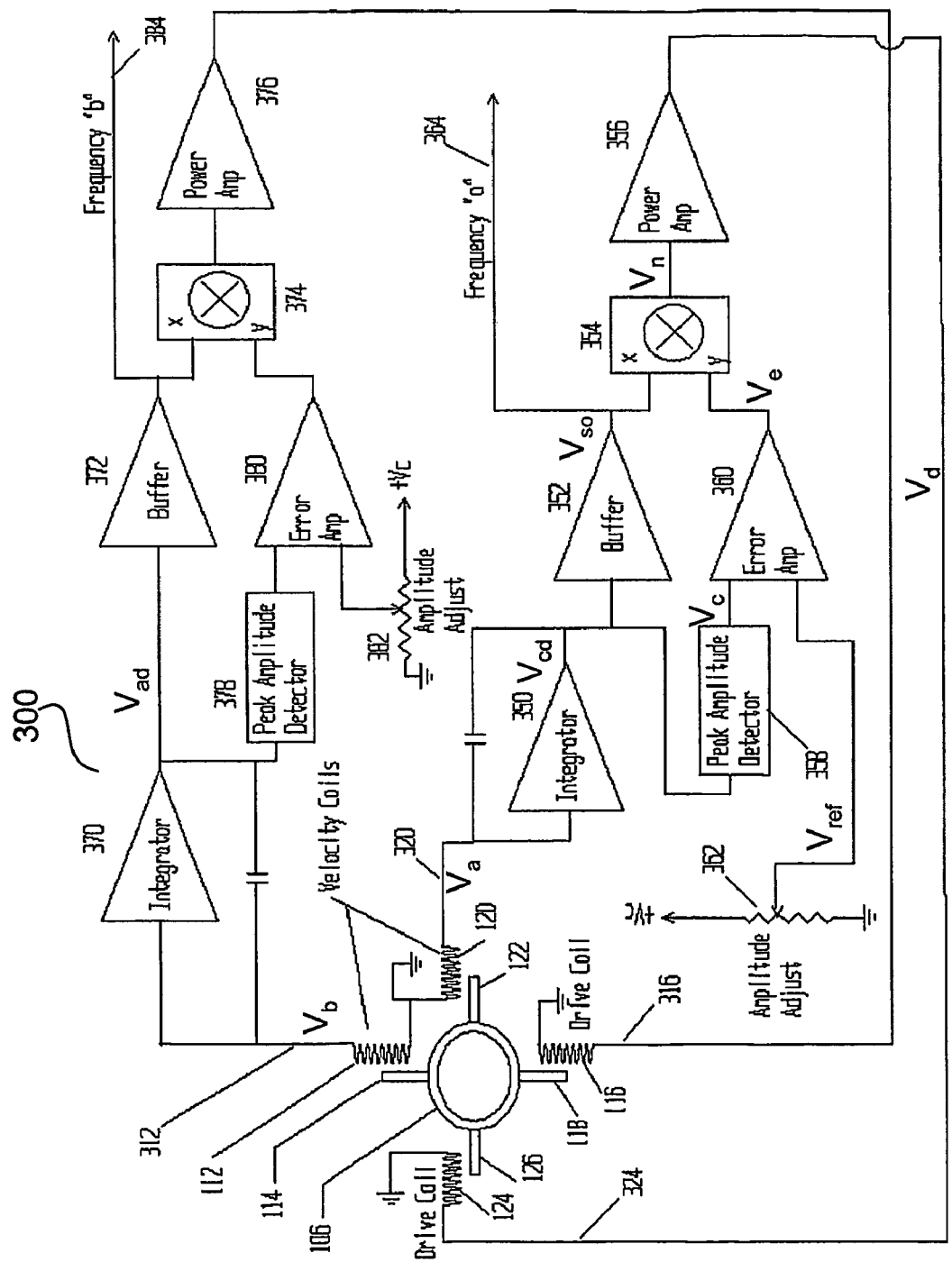
FIG. 3 shows a circuit for vibrating a conduit in two orthogonal directions in one embodiment of the invention.

FIG. 3 shows a circuit 300 for vibrating conduit 106 in two orthogonal directions, in one embodiment of the invention. Circuit 300 is also configured for detecting a frequency of conduit 106 resulting from the vibration. In one embodiment, a frequency signal $V_a$ from movement of magnet 122 within pickoff 122 is presented to integrator 350 via connection 320 for the a direction. Integrator 350 converts the sinusoidal velocity signal to a sinusoidal displacement signal $V_d$. The displacement signal $V_d$ is feed back to a drive coil 124 through a buffer amplifier 352, a multiplier 354, a power amplifier 356 and a connection 324 forming a closed loop electromechanical oscillator. The electromechanical oscillator frequency is approximately the resonant frequency for conduit 106.

Displacement control is useful to avoid fatigue overstress and to maintain conduit 106 within physical constraints of the coil arrangement shown in FIG. 2. Displacement control is accomplished by presenting the sinusoidal displacement signal $V_{cd}$ from integrator 350 to a peak amplitude detector 358. This peak amplitude detector 358 may determine the maximum amplitude of the time varying displacement signal and represents it as a DC output $V_c$.

Peak amplitude detector 358 output $V_c$ is presented to an error amplifier 360. Error amp 360 compares the output to a reference amplitude $V_{ref}$ set by amplitude adjust 362. The comparison is a DC representation of the deviation of the actual displacement relative to the level set by amplitude adjust 360. The output $V_e$ of the error amplifier 360 is presented to a Y input of a multiplier 354 where it is multiplied by the sinusoidal signal output $V_{so}$ from buffer 352. The multiplier 354 output $V_n$ is a sinusoidal signal where amplitude varies in direct proportion to tie error amplifier 360 output.

As an example, the maximum transverse amplitude or displacement of conduit 106 in the bending direction may be maintained at a predetermined level by controlling the output of peak amplitude detector 358. An increase in amplitude of the conduit 106 frequency signal causes an increase in the output of peak amplitude detector 358. Error amplifier 360 output $V_e$ will decrease as the peak amplitude detector 358 output $V_c$ exceeds the value $V_{ref}$ set by amplitude adjustment 362, reducing the Y input $V_e$ to the multiplier 354. Consequently, the amplitude of the signal $V_n$ presented to the power amplifier 356 is reduced as well as the power supplied to coil 124 through connection 324, thereby restoring conduit 106 vibrational amplitude. A decrease in conduit vibrational amplitude causes the reverse action to occur. The drive signal is increased until the tube displacement is restored to the level set by amplitude adjustment 362.

The aforementioned sequence of action is similar for the b direction. A velocity signal $V_b$ caused by the action of electromagnetic oscillator 119, as received by pickoff 114 is passed to integrator 370 via connection 312. A displacement signal $V_{ad}$ from integrator 370 is buffered by buffer amplifier 372 and the maximum displacement is determined by peak detector 378. The maximum displacement in the "b" direction is preset by an amplitude adjustment 382. The difference between the amplitude adjustment 382 and peak amplitude detector 378 is calculated by error amplifier 380 and passed to the Y input of multiplier 374. Multiplier 374 takes the output of buffer amplifier 372 and multiplies by the DC signal from error amplifier 380. Multiplier 374 output is amplified by power amplifier 376 and presented to a coil 116 through a connection 316. The resulting electromechanical oscillator maintains vibration in the "b" direction at controlled and sustained amplitude.

Sinusoidal signals from buffer 352 and from buffer 372 are passed onto the signal processing electronics (shown in FIG. 4) through connections 364 and connection 384. The frequency of the waveform is substantially identical to the frequency of vibration in the "a" and "b" directions.

By design, the amplitude of vibration, in both the "a" and "b" directions, should be as high as possible to optimize the SNR, but limited to avoid fatiguing conduit 106, and by the dimensional constraints shown in FIG. 2. The amplitude of vibration is a design parameter taking these and other considerations into account. The use of the described feedback technique shown in FIG. 2 is one of several ways to maintain resonance of conduit 106. Although other means may be used, those skilled in the art will recognize that the same operating principles apply as equivalent in generating "frequency a" and "frequency b" signals.

Figure 4:
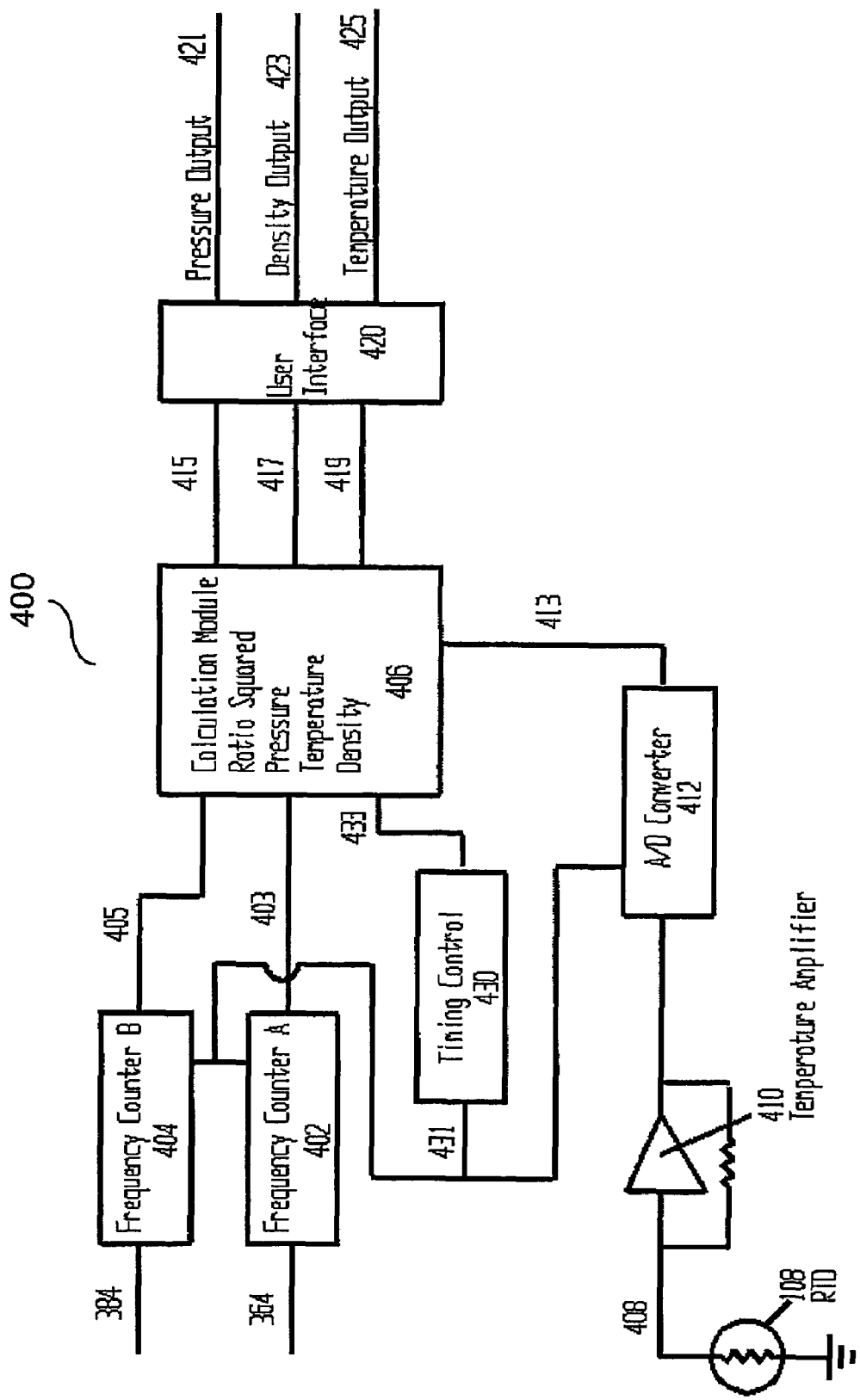
FIG. 4 is a block diagram of a system for calculating variables in one embodiment of the invention.

FIG. 4 is a block diagram of processing system 400 for calculating output values according to one embodiment. For example, system 400 may convert frequency signals a and b from buffer 352 and buffer 372 (both of FIG. 3) to output pressure 421, density 423, and temperature 425. Such a conversion may be performed according the principles of operation described herein above. Frequency counter A 402 converts the "frequency a" signal on connection 384 to a numeric or digital representation of frequency. The numerical representation is passed to calculation module 406 via connection 403. A frequency counter B 404 converts the "frequency b" signal on connection 384 to a numeric or digital representation of frequency. The numerical representation is passed to the calculation module 406 via connection 405.

Temperature measured by RTD 108 is conveyed to temperature amplifier 410 via connection 408 and converted to a numeric value by A/D converter 412. The numerical representation of temperature is passed to the calculation module 406 via connection 413.

A measurement complete signal 433 is generated by a timing control 430 taking in to account the status of frequency counter A 402, frequency counter B 404, and A/D converter 412 via a connection 431. For example, the measurement complete signal 433 flags the calculation module 406 as to when the numerical representations on connections 403, 405, and 413 are valid and calculation processing can proceed. For example, calculations may be valid when power consumption at coils 116 and 124 of FIG. 3 is essentially minimal and/or constant Calculation module 406 is programmably configured to calculate squared frequencies, frequency ratio, and average frequency squared terms, as described herein above. Predetermined calibration factors are used to convert these terms to pressure, density, and temperature outputs. Eqs. 2 and 3 are, for example, coded through firmware, hardware and/or software within calculation module 406. For example, calculation module 406 may be a general purpose processor configured for processing software instructions to operate in accordance with the invention. Processors, software and firmware are known to those skilled in the art.

Calculated results for pressure 421, density 423, and temperature 425 are presented via connections 415, 417, and 419 to a user interface 420. User interface 420 makes pressure, density, and temperature measurements available for monitoring, further process control and/or other actions identified by a user through pressure output 421, density output 423, and temperature output 425, respectively. Alternatively, outputs 421, 423, 425 may be used as automated process controls affecting fluid F.

Figure 5:
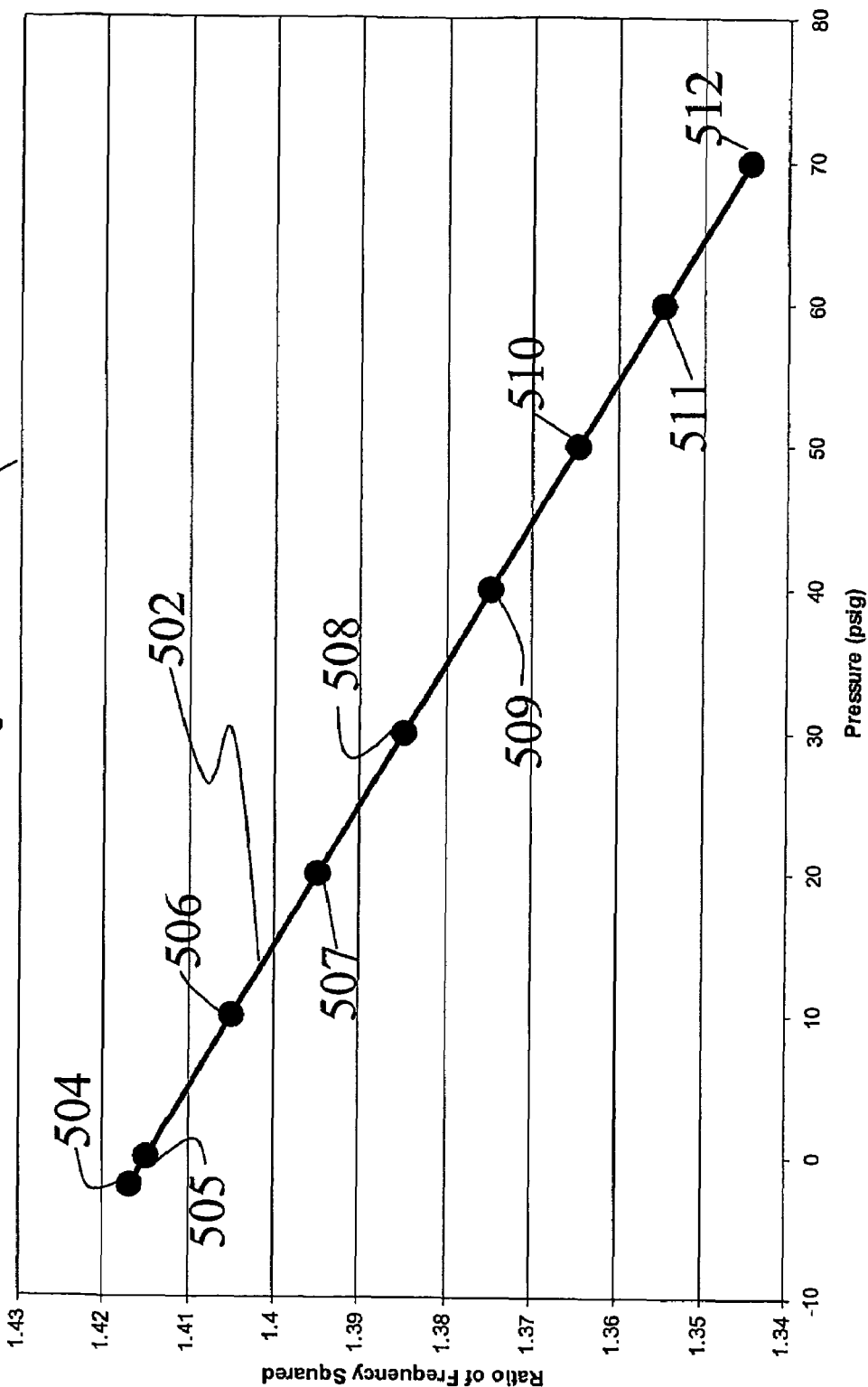
FIG. 5 is a graph showing frequency ratio as it relates to pressure in one embodiment of the invention.

FIG. 5 is a graph 500 showing an exemplary relationship between frequency ratio squared and pressure. In this exemplary embodiment, data points 504, 505, 506, 507, 508, 509, 510, 511, and 512 are collected by setting the pressure inside a conduit 106 to the abscissa values shown and vibrating conduit 106 to determine a frequency ratio, for example, as shown if Eq. 2. Frequency values at connection 403 and connection 405 (both of FIG. 4) are determined for each pressure setting and used to calculate ordinate values of ratio of frequency squared. By way of example, a trace 502 is created using least squares regression to generate the best-fit, straight, line through the data. A multiple axis fit may also be used as second or third order to provide a best fit, for example, accommodating system deviations from the theoretical norm arising from the presence of oscillators 114, 118, 122, 126, or inconsistent thicknesses, dents and the like in conduit 106. Trace 502 shows correlation with data points 504, 505, 506, 507, 508, 509, 510, 511, and 512 indicating a substantially linear relationship between pressure and frequency ratio squared. Those skilled in the art should readily recognize that other curve fitting algorithms may be utilized. The intersection of trace 502 with data points 504 and 505 indicate that trace 502 can be used to determine pressure under vacuum conditions where the pressure inside conduit 106 is less than the pressure applied to the outside. By way of example, the process as outlined could be used to determine appropriate calibration factors required for a calibration module 406 of FIG. 4. Fluid F may, for example, be a gas, liquid, slurry, emulsion, or aerosol.

Figure 6:
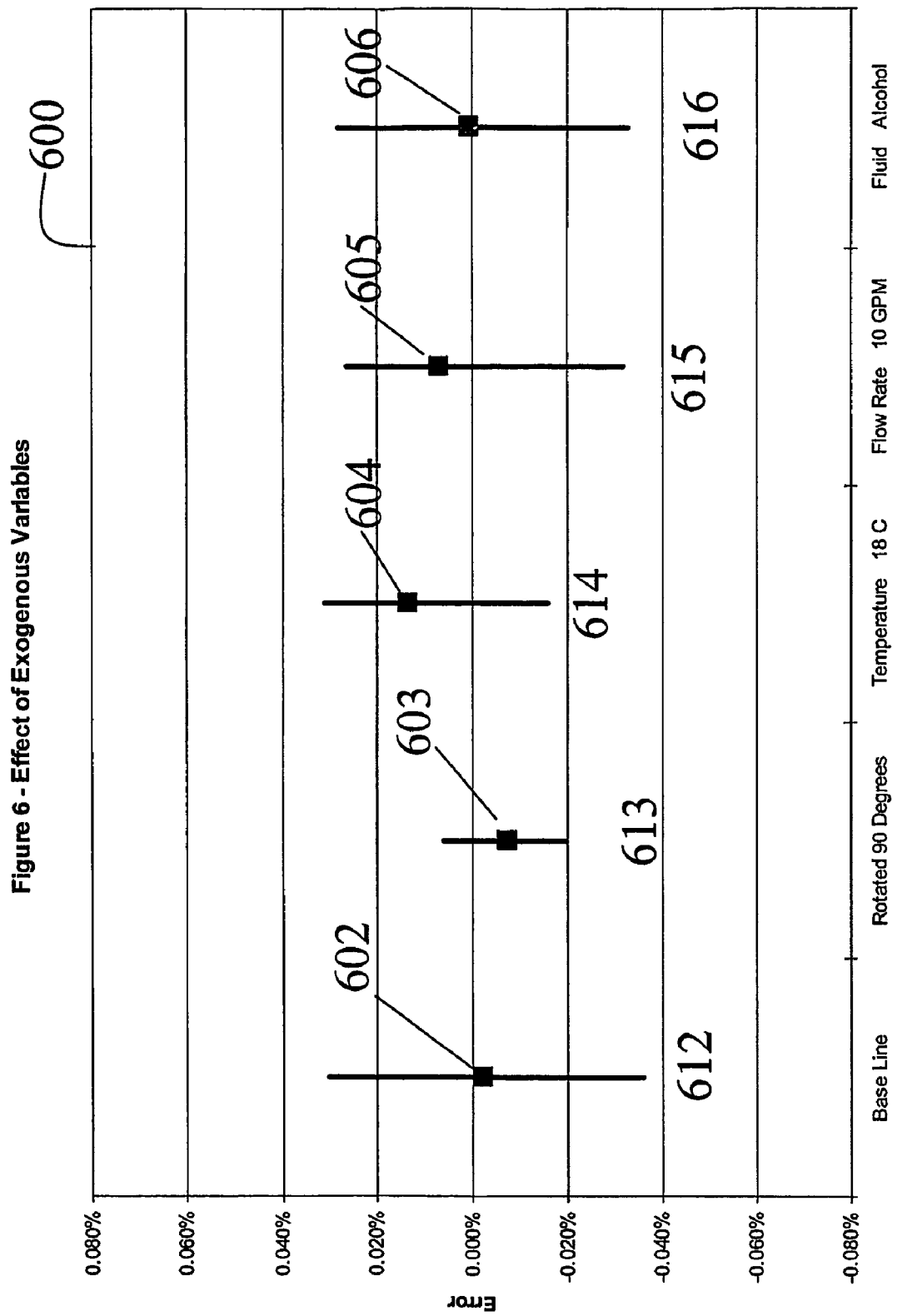
FIG. 6 is a graph showing immunity to exogenous variables in one embodiment of the invention.

FIG. 6 is a graph 600 showing immunity to exogenous variables in one embodiment of the invention. For example, graph 600 shows a relationship between pressure measurement repeatability errors and certain operating conditions. Such operating conditions include baseline, selected installation (i.e., 90 degree rotated installation), fluid temperature, fluid flow rate, and fluid type (i.e., alcohol) operating conditions. In this exemplary embodiment, data points 602, 603, 604, 605, and 606 represent averages of actual error measurements associated with the abscissa conditions identified. The length of lines 612, 613, 614, 615, and 616 indicate the range of errors observed over multiple pressure measurements. Data point 602 and line 612 represent error data for baseline conditions where the fluid was water, flowed at zero Gallons Per Minute, at a temperature of 25 degrees Celsius, and 0 degrees rotation. Comparison of data points 603, 604, 605, and 606 and lines 613, 614, 615, and 616 line to line 612 suggest that the pressure measurement is substantially independent of changes in orientation, fluid type, temperature, and flow rate. Thus, these results show an advantage over the prior art, namely, improve accuracy without additional cost due to complex calibration. Calibrated accuracy is maintained under most actual operating conditions.

Figure 7:
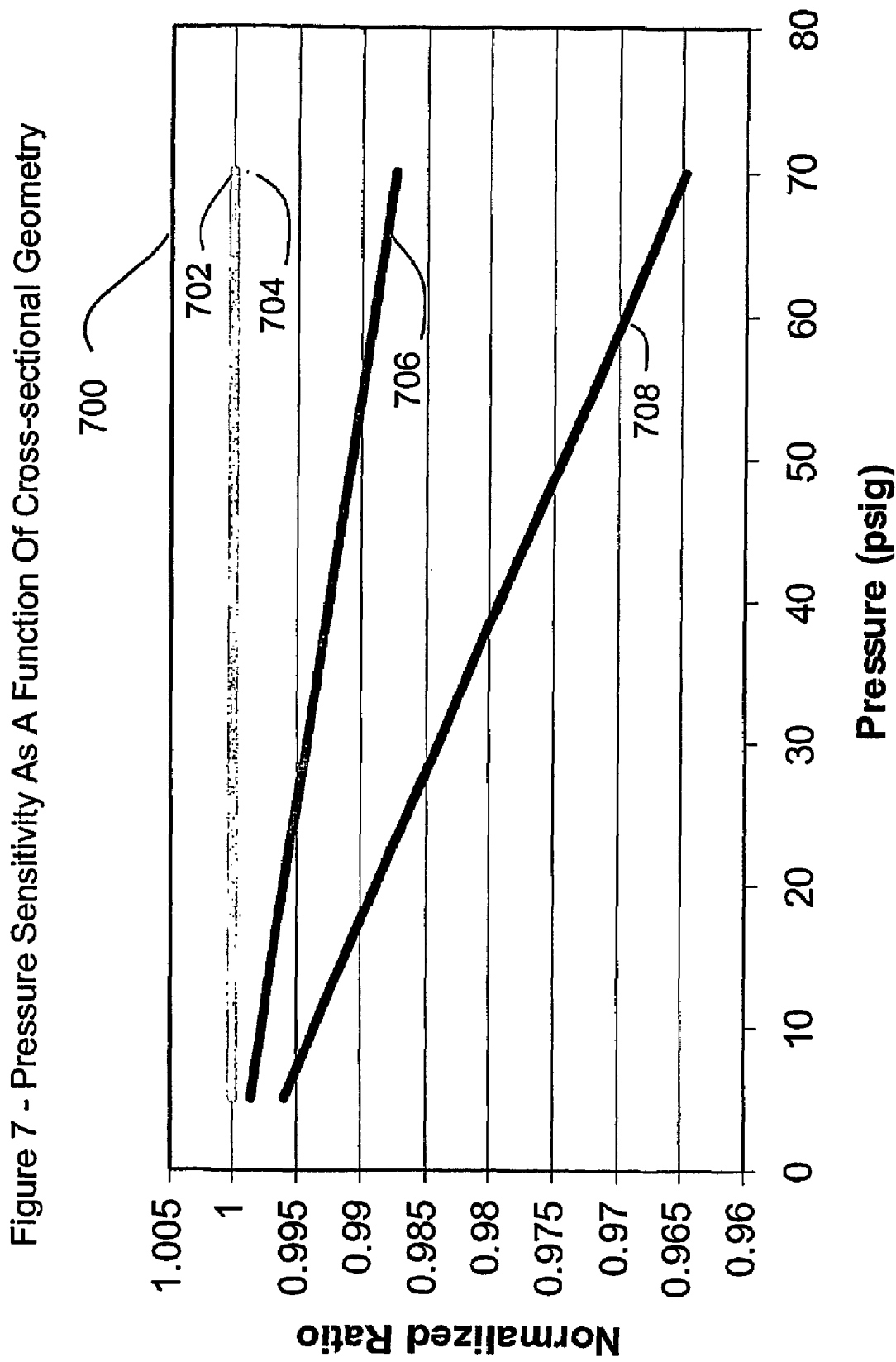
FIG. 7 is a graph showing pressure sensitivity as a function of conduit geometry in one embodiment of the invention.

FIG. 7 is a graph 700 showing pressure sensitivity as a function of conduit geometry in one embodiment of the invention. Graph 700 shows an exemplary relationship between fluid pressure in pounds per square inch gauge (PSIG) and a normalized ratio of frequency squared. Traces 702, 704, 706, and 708 were derived from actual measurements taken on conduits of increasingly elliptical cross-sections. For example, trace 702 shows the change in normalized frequency ratio squared as a function of pressure where the conduit cross section is approximately circular. The trace 702 shows a slope that is substantially zero indicating limited pressure sensitivity. Other traces have a/b ratios that affect pressure sensitivity in other ways, such as trace 704 where the a/b ratio was 1.01, trace 706 where the a/b ratio was 1.10, and trace 708 where the a/b ratio was 1.28.

Traces 704, 706, and 708 were developed for increasingly elliptical cross sections using the same measurement techniques applied in the development of trace 702. As the conduit becomes more elliptical, pressure sensitivity increases as indicated by the increasing slope of traces 704, 706, and 708. In this exemplary embodiment, conduits that are substantially circular show limited change in frequency with applied pressure. As ellipticity increases, pressure sensitivity improves yielding greater separation of a pressure measurement from other variables. The ability to increase pressure sensitivity by altering the cross section of the conduit represents a distinct advantage over the prior art. As used herein, ellipticity is a shape parameter describing the degree that a cross section is elliptical, where a circular cross section has essentially zero ellipticity and ellipticity increases with increasing a to b ratio. Sensitivity also increases as the thickness of walls in conduit 106 decreases.

Figure 8:
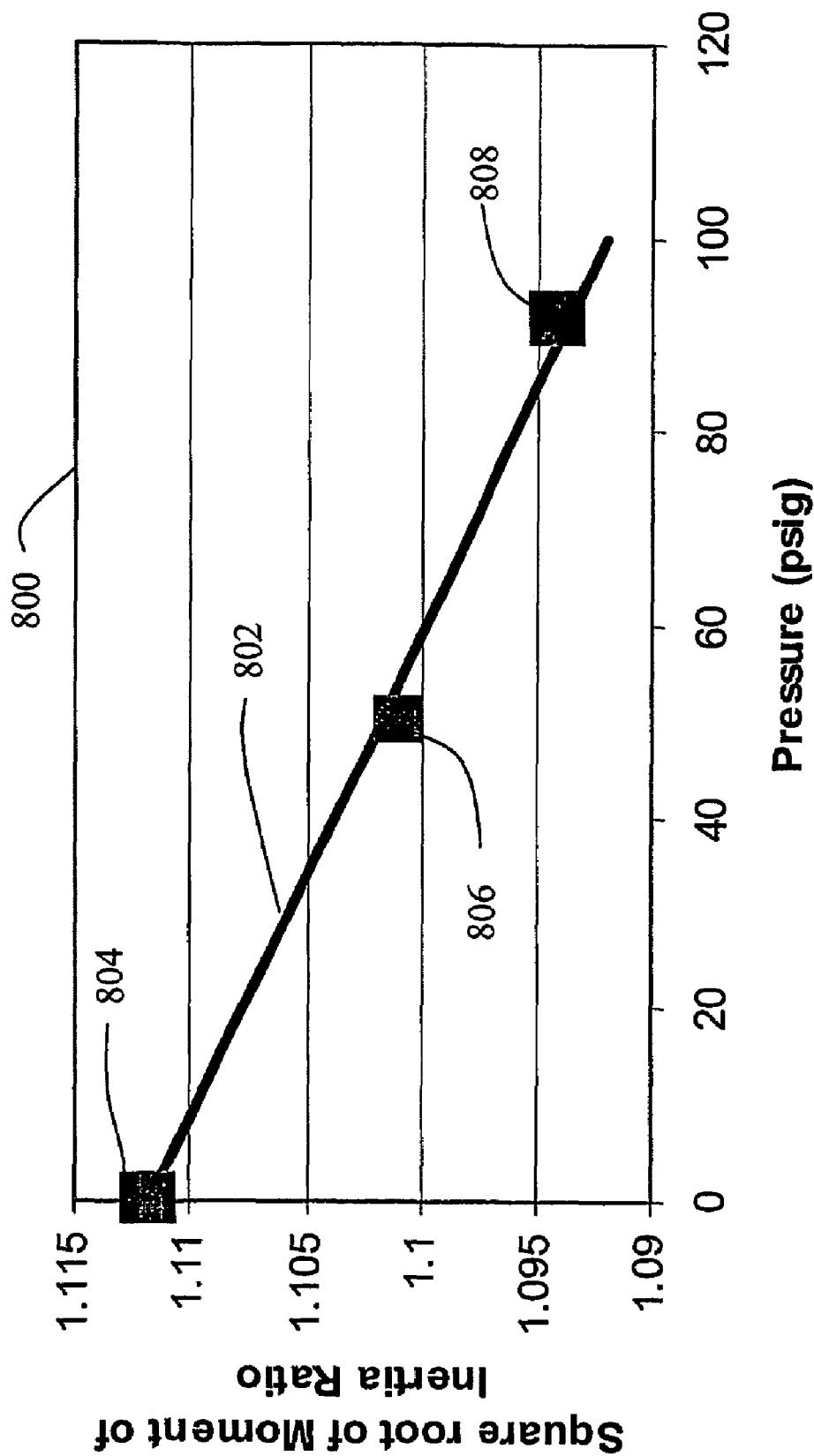
FIG. 8 is a graph showing the relationship between pressure and the square root of the ratio of inertial moments in one embodiment of the invention.

FIG. 8 is a graph 800 showing the relationship between pressure and the square root of the ratio of inertial moments in one embodiment of the invention. For example, trace 802 shows that the calculated relationship between pressure and the square root of the $I_a$ to $I_b$ ratio. In this exemplary embodiment, Eq. 3, 4, and 5 are determined for an elliptical conduit, such as conduit 106 of FIGS. 1 and 2, of approximately 12 inches in length, with an a to b ratio of 1.15. These equations were solved and trace 802 generated assuming pressure in the range of 0 and 100 pounds per square inch gauge applied to the inside of the conduit. The modeling illustrated by trace 802 was physically verified through data points 804, 806, and 808. For example, data points 804, 806, and 808 represent actual measurements and conform to the calculated relationship between square root of $I_a$ to $I_b$ ratio and pressure.

Figure 9:
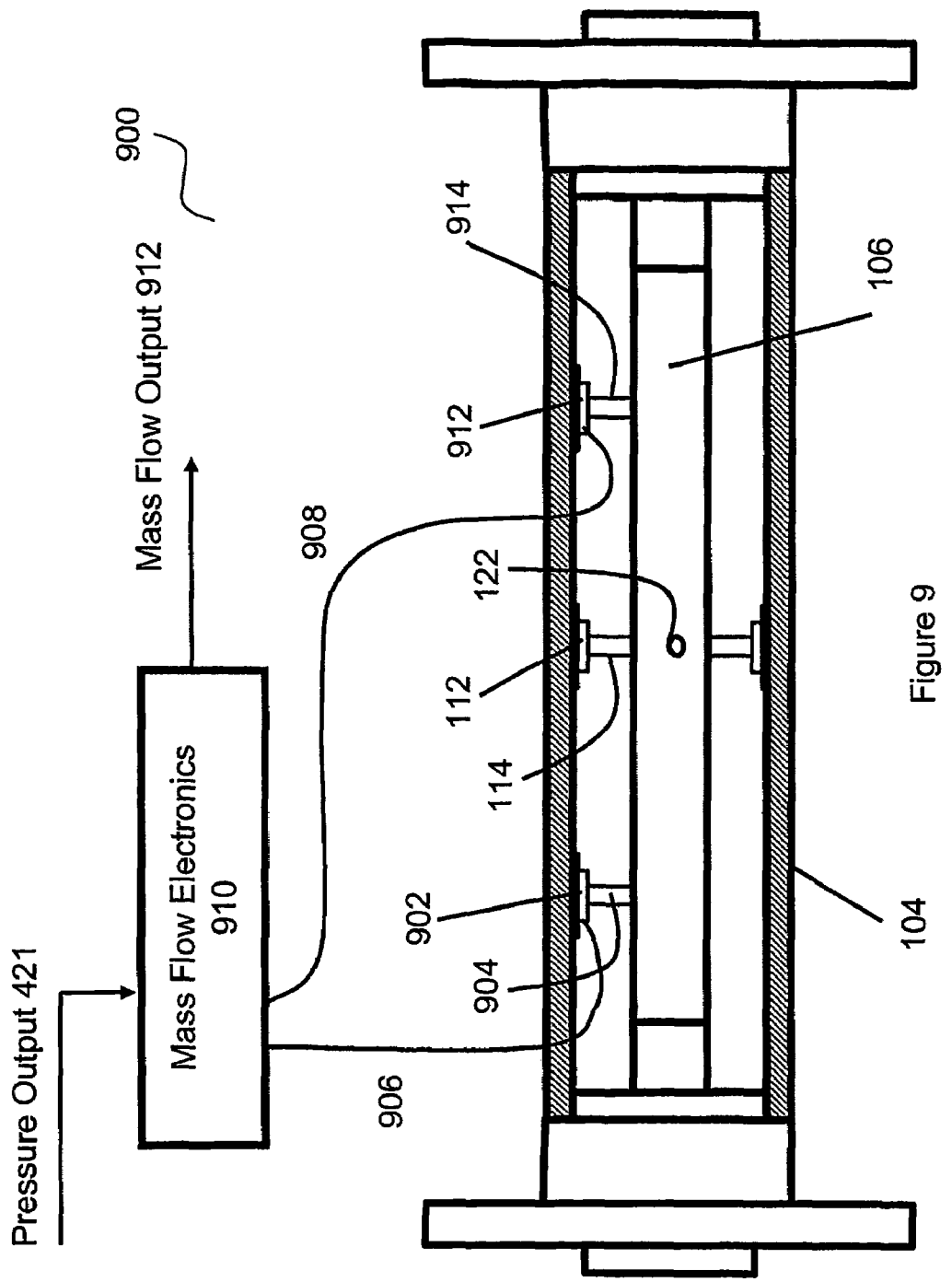
FIG. 9 shows a sensor with mass flow measurement capability in one embodiment of the invention.

FIG. 9 shows sensor 900 with mass flow measurement capability in one embodiment. For example, sensor 900 may include a mass flow measurement capability through the addition of two additional velocity sensors and associated mass flow electronics. In this exemplary embodiment, a first electromagnetic oscillator pickoff 902 and a second electromagnetic oscillator pickoff 912 and magnet 914 may be added to conduit 106 perpendicular to the major cross sectional axis to assist in measuring mass flow. Electromagnetic oscillators 902 and 912 attach to housing 104 and are constructed to allow substantially free movement of conduit 106. Signals from the first and the second velocity sensors are conveyed to mass flow electronics 910 via connection 906 and connection 908. Mass flow electronics 910 are configured to determine a time difference (Δt) between first and second velocity crossing a predetermined level. Pressure output signal 421 is used by mass flow electronics 910 to determine the pressure correction factor ($F_c$). Eq. 11, coded through hardware, firmware, or software, is solved and a calculated mass flow rate output 912 is made available for monitoring, process control, or other uses defined by a user via connection 912.

In another embodiment, electromagnetic oscillator pickoffs 902 and 912 may be located on the conduit 106 perpendicular to the minor cross sectional axis. In yet another embodiment a velocity sensor formed by electromagnetic oscillator pickoff 114, 126 (both of FIG. 2) maybe used in lieu of either first velocity sensor or second velocity sensor.

Advantages of the apparatus and methods described herein include cost effective manner in which to provide accurate pressure measurements of a fluid. For example, a sensor as described herein uses a ratio of frequencies detected as a result of vibrating a conduit. The ratio of frequencies may then be used to determine a pressure of the fluid by using substantially the same circuitry of existing sensor systems, thereby alleviating a need for additional complex signal processing and/or circuitry. Additionally, since the sensor uses typical structures for vibrating the conduit, the sensor may determine other fluid variables, such as density and mass flow rate of the fluid, using known methods.

While the invention has been illustrated and described in the drawings and foregoing description, such illustration and description is to be considered as exemplary and not restrictive in character. One embodiment of the invention and minor variants thereof have been shown and described. Protection is desired for all changes and modifications that come within the spirit of the invention. Those skilled in the art will appreciate variations of the above-described embodiments that fall within the scope of the invention. As a result, the invention is not limited to the specific examples and illustrations discussed above, but only by the following claims and their equivalents.

The invention claimed is:

1. A sensor (100), characterized in that the sensor comprises:
   a conduit (106) configured for conveying a material (F), the conduit presenting an axial length,
   the conduit having a noncircular cross-section of major axis (a) and minor axis (b) of respective dimensions (a) and (b) each taken as perpendiculars with respect to the axial length, wherein the cross-section tends to become slightly more circular as pressure internal to the conduit is increased;
   a vibrator (118,126) configured for vibrating the conduit along a first cross-sectional axis and for vibrating the conduit along a second cross-sectional axis;
   a sensor (114,122) configured for detecting a first frequency along the first cross-sectional axis (a) and for detecting a second frequency along the second cross-sectional axis (b); and
   a processor (400) configured for determining a pressure of the material based on a ratio of the first frequency and the second frequency;
   wherein the ratio is related to the pressure through first and second inertial moments according to an equation having a form of $$\frac{(firstfrequency)^2}{(secondfrequency)^2} = \frac{I_a}{I_b}, \text{where} \qquad \text{(Eq. 2)}$$

$I_a$ is the first inertial moment and $I_b$ is the second inertial moment.

2. The sensor of claim 1, wherein the conduit comprises a cross-section selected from one of an elliptical shape and an oval shape.

3. The sensor of claim 1, wherein the first inertial moment has a form of $$I_a = \frac{\pi}{4}((b+\delta_b)(a+\delta_a)^3 - ((b+\delta_b-t)(a+\delta_a-t)^3), \text{ where} \quad \text{(Eq. 5)}$$

b is a length of one half the second cross-sectional axis, $\delta_b$ is a displacement for the second cross-sectional axis, a is a length of one half the first cross-sectional axis, $\delta_a$ is a displacement for the first cross-sectional axis and t is a conduit wall thickness.

4. The sensor of claim 1, wherein the pressure linearly corresponds (500) to the ratio of the first and the second frequencies.

5. The sensor of claim 1, wherein the conduit is elastically deformable to change a length of the second cross-sectional axis based on the pressure of the material.

6. The sensor of claim 1, wherein the processor further comprises a calculation module (406) configured for determining a density of the material from one of:
   a calculation of the pressure, a pressure compensation factor, and one of the first frequency and the second frequency, and
   a calculation of an average of the first frequency and the second frequency.

7. The sensor of claim 6, further comprising:
   a temperature sensor (108) configured for detecting a temperature of the material conveyed through the conduit and for generating a temperature control signal for processing by the processor; and
   a timing controller (430) configured for synchronizing the processing of the temperature control signal with the determining of the density.

8. The sensor of claim 1, further comprising a frequency sensor (114, 122) configured for detecting a phase difference in at least one of the first and the second frequencies, wherein the processor is further adapted to determine a mass flow rate of the material based on the phase difference.

9. A method of measuring a property of a material (F) conveyed through a conduit (106), the conduit presenting an axial length and a noncircular cross-section of major axis (a) and minor axis (b) of respective dimensions (a) and (b) each taken as perpendiculars with respect to the axial length, wherein the cross-section tends to become slightly more circular as pressure internal to the conduit is increased, the method characterized in that the method comprises:
   vibrating the conduit along a first cross-sectional axis (a);
   vibrating the conduit along a second cross-sectional axis (b);
   detecting a first resonant frequency along the first cross-sectional axis in response to vibrating the conduit at the first cross-sectional axis;
   detecting a second resonant frequency at the second cross-sectional axis in response to vibrating the conduit along the second cross-sectional axis; and
   determining a pressure of the material based on a ratio of the first resonant frequency and the second resonant frequency;
   wherein determining comprises determining a first inertial moment and a second inertial moment according to an equation having a form of $$\frac{(firstfrequency)^2}{(secondfrequency)^2} = \frac{I_a}{I_b}, \text{ where} \quad \text{(Eq. 2)}$$

$I_a$ is the first inertial moment and $I_b$ is the second inertial moment.

10. The method of claim 9, wherein vibrating the conduit along the first cross-sectional axis comprises vibrating the conduit along the first cross-sectional axis of an elliptically-shaped cross-section of the conduit.

11. The method of claim 9, wherein vibrating the conduit along the first cross-sectional axis comprises vibrating the conduit along the first cross-sectional axis of an oval-shaped cross-section of the conduit.

12. The method of claim 9, wherein determining further comprises determining the first inertial moment according to an equation having a form of $$I_a = \frac{\pi}{4}((b+\delta_b)(a+\delta_a)^3 - ((b+\delta_b-t)(a+\delta_a-t)^3), \text{ where} \quad \text{(Eq. 5)}$$

b is a length of one half the second cross-sectional axis, $\delta_b$ is a displacement for the second cross-sectional axis, a is a length of one half the first cross-sectional axis, $\delta_a$ is a displacement for the first cross-sectional axis and t is a conduit wall thickness.

13. The method of claim 9, wherein determining comprises determining the pressure by linearly corresponding the pressure to a ratio of the first and the second frequencies.

14. The method of claim 9, further comprising conveying the material through the conduit, wherein conveying comprises elastically deforming the conduit to change a length of the second cross-sectional axis based on the pressure of the material.

15. The method of claim 9, wherein detecting comprises converting the first resonant frequency and the second resonant frequency into digital representations of the first resonant frequency and the second resonant frequency.

16. The method of claim 15, wherein determining comprises processing the digital representations of the first resonant frequency and the second resonant frequency to determine the pressure of the material based on the squared ratio of the first resonant frequency and the second resonant frequency.

17. The method of claim 9, further comprising determining a density of the material from one of:
   a calculation of the pressure, a pressure compensation factor, and one of the first frequency and the second resonant frequency (Eq. 9); and
   a calculation of an average of the first resonant frequency and the second frequency (Eq. 8).

18. The sensor of claim 17, further comprising: detecting a temperature of the material and generating a temperature control signal in response to detecting the temperature; and
   processing the temperature control signal with the digital representations of the first resonant frequency and the second resonant frequency in a substantially synchronous manner to determine the density of the material.

19. The method of claim 9, further comprising:
   detecting a phase difference in at least one of the first and the second resonant frequencies (Eq. 10); and
   determining a mass flow rate of the material based on the phase difference (Eq.11).

20. A sensor (100), characterized in that the sensor comprises:
- a vibrator (118, 126) configured for vibrating the conduit along a first cross-sectional axis and for vibrating the conduit along a second cross-sectional axis;
- a sensor (114,122) configured for detecting a first frequency along the first cross-sectional axis (a) and for detecting a second frequency along the second cross-sectional axis (b); and
- a processor (400) configured for determining a pressure of the material based on a ratio of the first frequency and the second frequency
- wherein the ratio is related to the pressure through first and second inertial moments according to an equation having a form of $$\frac{(firstfrequency)^2}{(secondfrequency)^2} = \frac{I_a}{I_b}, \text{ where} \qquad (\text{Eq. 2})$$

$I_a$ is the first inertial moment and $I_b$ is the second inertial moment.

21. The sensor of claim 20, wherein the first inertial moment has a form of $$I_a = \frac{\pi}{4}((b+\delta_b)(a+\delta_a)^3 - ((b+\delta_b-t)(a+\delta_a-t)^3), \text{ where} \qquad (\text{Eq. 5})$$

b is a length of one half the second cross-sectional axis, $\delta_b$ is a displacement for the second cross-sectional axis, a is a length of one half the first cross-sectional axis, $\delta_a$ is a displacement for the first cross-sectional axis and t is a conduit wall thickness.

22. A method of measuring a property of a material (F) conveyed through a conduit (106), characterized in that the method comprises:
- vibrating the conduit along a first cross-sectional axis (a);
- vibrating the conduit along a second cross-sectional axis (b);
- detecting a first resonant frequency along the first cross-sectional axis in response to vibrating the conduit at the first cross-sectional axis;
- detecting a second resonant frequency at the second cross-sectional axis in response to vibrating the conduit along the second cross-sectional axis; and
- determining a pressure of the material based on a ratio of the first resonant frequency and the second resonant frequency,
- wherein determining comprises determining a first inertial moment and a second inertial moment according to an equation having a form of $$\frac{(firstfrequency)^2}{(secondfrequency)^2} = \frac{I_a}{I_b}, \text{ where} \qquad (\text{Eq. 2})$$

$I_a$ is the first inertial moment and $I_b$ is the second inertial moment.

23. The method of claim 22, wherein determining further comprises determining the first inertial moment according to an equation having a form of $$I_a = \frac{\pi}{4}((b+\delta_b)(a+\delta_a)^3 - ((b+\delta_b-t)(a+\delta_a-t)^3), \text{ where} \qquad (\text{Eq. 5})$$

b is a length of one half the second cross-sectional axis, $\delta_b$ is a displacement for the second cross-sectional axis, a is a length of one half the first cross-sectional axis, $\delta_a$ is a displacement for the first cross-sectional axis and t is a conduit wall thickness.

* * * * *